(12) United States Patent
Yu et al.

(10) Patent No.: US 12,141,962 B2
(45) Date of Patent: Nov. 12, 2024

(54) METHODS AND SYSTEMS FOR IMPROVED ABNORMALITY DETECTION IN MEDICAL IMAGING DATA

(71) Applicant: Siemens Healthcare GmbH, Erlangen (DE)

(72) Inventors: Xin Yu, Nashville, TN (US); Bin Lou, Princeton, NJ (US); Bibo Shi, Monmouth Junction, NJ (US); David Jean Winkel, Basel (CH); Ali Kamen, Skillman, NJ (US); Mamadou Diallo, Plainsboro, NJ (US); Tongbai Meng, Ellicott City, MD (US); Afshin Ezzi, Zug (CH)

(73) Assignee: Siemens Healthineers AG, Erlangen (DE)

( * ) Notice: Subject to any disclaimer, the term of this patent is extended or adjusted under 35 U.S.C. 154(b) by 785 days.

(21) Appl. No.: 17/220,211

(22) Filed: Apr. 1, 2021

(65) Prior Publication Data

US 2021/0312615 A1    Oct. 7, 2021

(30) Foreign Application Priority Data

Apr. 1, 2020 (EP) .................................... 20167487

(51) Int. Cl.
  *G06T 7/00* (2017.01)
  *G06T 7/11* (2017.01)
  *G16H 30/40* (2018.01)
(52) U.S. Cl.
  CPC .............. *G06T 7/0012* (2013.01); *G06T 7/11* (2017.01); *G16H 30/40* (2018.01);
  (Continued)

(58) Field of Classification Search
  CPC ..................... G06T 7/0012; G06T 7/11; G06T 2207/20081; G06T 2207/20084;
  (Continued)

(56) References Cited

U.S. PATENT DOCUMENTS 8,472,684 B1 * 6/2013 Periaswamy ........ A61B 6/5235
                                              382/128
2018/0240233 A1 * 8/2018 Kiraly ................... G06T 7/0012
(Continued)

FOREIGN PATENT DOCUMENTS

WO    2019238804 A1    12/2019

OTHER PUBLICATIONS

Litjens, Geert et al. "A Survey on Deep Learning in Medical Image Analysis" Medical Image Analysis, vol. 42, pp. 60-88, 2017, XP080747655, ISSN: 1361-8415, DOI: 10.1016/J.MEDIA.2017.07.005.
(Continued)

*Primary Examiner* — Ping Y Hsieh
*Assistant Examiner* — Jose M Torres
(74) *Attorney, Agent, or Firm* — Banner & Witcoff Ltd.

(57) ABSTRACT

In an method for training artificial intelligence entities (AIE) for abnormality detection, medical imaging data of the human organ is provided as training data having training samples, the medical imaging data including imaging results from different types of imaging techniques for each training sample of the training data, a pre-trained or randomly initialized AIE is provided, and the AIE is trained using the provided training samples. The training may include, for at least one training sample, a first loss function for a sub-structure of the AIE is calculated independently of a first spatial region of the human organ, and, for a training sample, a second loss function for a sub-structure of the AIE is calculated independently of a second spatial region of the human organ. The AIE may be trained using the calculated first loss function and the calculated second loss function.

19 Claims, 5 Drawing Sheets

(52) U.S. Cl.
CPC ............... *G06T 2207/20081* (2013.01); *G06T 2207/20084* (2013.01); *G06T 2207/20221* (2013.01); *G06T 2207/30081* (2013.01)

(58) Field of Classification Search
CPC . G06T 2207/20221; G06T 2207/30081; G06T 2207/10028; G16H 30/40
See application file for complete search history.

(56) References Cited

U.S. PATENT DOCUMENTS

| | | | |
|---|---|---|---|
| 2019/0304092 A1* | 10/2019 | Akselrod-Ballin | .... G06N 3/084 |
| 2019/0370965 A1* | 12/2019 | Lay | ........................ G06N 20/00 |
| 2020/0012761 A1 | 1/2020 | El-Baz et al. | |
| 2020/0278408 A1* | 9/2020 | Sung | .................... G06V 10/764 |
| 2020/0401843 A1* | 12/2020 | Peng | .................... A61B 5/4842 |
| 2020/0402236 A1* | 12/2020 | Courot | ................. A61B 8/4416 |
| 2021/0248736 A1* | 8/2021 | Kamen | ................. G06F 18/214 |
| 2022/0215537 A1* | 7/2022 | Moreto Pereira | ......... G06T 7/11 |

OTHER PUBLICATIONS

Radiology Assistant; "Prostate Cancer—PI-RADS v2"; http://www.radiologyassistant.nl/en/p59987056acbb4/prostate-cancer-pi-rads-v2.html; Aug. 2018.

Tsehay, Yohannes K. et. al.; "Convolutional neural network based deep-learning architecture for prostate cancer detection on multiparametric magnetic resonance images"; Proc. SPIE 10134, Medical Imaging 2017: Computer-Aided Diagnosis, 1013405 (Mar. 3, 2017).

Taghanaki S. et al: Deep Semantic Segmentation of Natural and Medical Images: A Review11 , arxiv.org, Cornell University Library, 201 Olin Library Cornell University Ithaca, NY 14853, Oct. 16, 2019 (Oct. 16, 2019), XP081516776, * the whole document *; 2019.

Dinggang Shen et al.; "Deep Learning in Medical Image Analysis"; Guorong Wu, and Heung-Il Suk 1 Department of Radiology; University of North Carolina, Chapel Hill & 2Department of Brain and Cognitive Engineering, Korea University Annu. Rev. Biomed. Eng. 2017; vol. 19; pp. 221-248.

Cao, R. et al.; "Joint Prostate Cancer Detection and Gleason Score Prediction in mp-MRI via FocalNet,"; in IEEE Transactions on Medical Imaging; vol. 14, No. 8, Aug. 2015; doi: 10.1109/TMI.2019.2901928.

He, Kaiming, et al.; "Delving deep into rectifiers: Surpassing human-level performance on imagenet classification."; Proceedings of the IEEE international conference on computer vision; 2015.

Yang Xin et al: Co-trained convolutional neural networks for automated detection of prostate cancer in multi-parametric MRI11 , Medical Image Analysis, vol. 42, Aug. 24, 2017 (Aug. 24, 2017), pp. 212-227, XP085240557, ISSN: 1361-8415, DOI: 10.1016/J.MEDIA.2017.08.006; pp. 216, line 22; figures 1, 3, 5, 6 * * section 2 *; 2017.

European Search Report Dated Sep. 18, 2020, Application No. 20167487.6.

* cited by examiner

METHODS AND SYSTEMS FOR IMPROVED ABNORMALITY DETECTION IN MEDICAL IMAGING DATA

CROSS REFERENCE TO RELATED APPLICATIONS

This patent application claims priority to European Patent Application No. 20167487.6, filed Apr. 1, 2020, which is incorporated herein by reference in its entirety.

BACKGROUND

Technical Field

The present disclosure relates to methods for training an artificial intelligence entity, AIE, for detecting abnormalities such as lesions in medical imaging data of a human organ, in particular a prostate. Moreover, the disclosure relates to methods for detecting abnormalities in such medical imaging data, in particular using an artificial intelligence entity, AIE. The disclosure also relates to devices for detecting abnormalities in such medical imaging data.

Related Art

Imaging techniques such as magnetic resonance imaging, MRI, computed tomography, CT, and so on are more and more used for diagnostic tasks. Different imaging techniques are differently suitable for imaging different organs so that often for one type of organ one type of imaging technique is dominant, i.e. is predominantly used and/or is best used for diagnostics.

Some organs, in particular the human prostate, have different regions which respond differently to different medical imaging techniques. For example, a human prostate is divided into, among others, a peripheral zone, PZ, and a transition zone, TZ. The transition zone, TZ, surrounds the prostatic urethra and enlarges in aging men as a result of benign prostatic hyperplasia. The peripheral zone, PZ, is situated on the posterior and lateral side of the prostate, surrounding the transition zone.

Medical imaging techniques for detecting lesions within the prostate are usually different types (or: series) of MRI (Magnetic Resonance Imaging) scans. For the prostate, typical MRI scans comprise T2-weighted MRI scans (T2W), diffusion-weighted imaging (DWI) and dynamic contrast-enhanced (DCE) imaging. These types of MRI scans, in particular the first two, are also used in the PI-RADS assessment categories. Whenever PI-RADS is mentioned herein, it is referred to the "Prostate Cancer—PI-RADS v2" document by Rhiannon van Loenhout, Frank Zijta, Robin Smithuis and Ivo Schoots, publication date 2018 Aug. 1, available e.g. at the URL: http://radiologyassitant.nl/abdomen/prostate-cancer-pi-rads-v2. However, it shall be understood that also future version of PI-RADS may be similarly applied.

A combination of the results of multiple types of MRI scans is sometimes designated as a "multiparametric MRI", wherein "multiparametric" refers to the different parameter settings with which the respective MRI scan is performed. PI-RADS, for example, designates a combination of T2-weighted, diffusion weighted and dynamic contrast-enhanced imaging as a "multiparametric MRI". Based on the results of multiparametric MRIs, PI-RADS assessment categories are based which are used for standardized acquisition, interpretation and reporting of prostate MRIs. The PI-RADS categories range from "PI-RADS 1" (very low-clinically significant cancer highly unlikely) to "PI-RADS 5" (clinically significant cancer highly likely), wherein a clinically significant prostate cancer is defined as a tumor with a Gleason score of 7 or more.

T2W imaging is the primary determining sequence (i.e. scan) to assign the PI-RADS category in the transition zone, TZ. On the other hand, diffusion-weighted imaging (in particular DWI ADC) is the primary determining sequence to assign the PI-RADS assessment category for the peripheral zone, PZ.

In the international publication WO 2019/238804 A1, various advantageous methods and variants for detecting and localizing abnormalities in medical images are described.

However, hitherto known attempts of employing deep learning for organs that happen to comprise different spatial regions (e.g. transition zone, TZ and peripheral zone, PZ, in case of the prostate) responding differently to different types of medical imaging scans neglect information about these different spatial regions.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

FIG. 1 shows a schematic flow diagram illustrating a method for training an artificial intelligence entity according to an exemplary embodiment;

FIG. 2 schematically illustrates the steps of the method of FIG. 1 according to an exemplary embodiment;

FIG. 3 shows a schematic flow diagram illustrating a method for detecting abnormalities within medical imaging data according to an exemplary embodiment;

FIG. 4 schematically illustrates the steps of the method of FIG. 3 according to an exemplary embodiment;

FIG. 5 shows a schematic flow diagram illustrating a method for training an artificial intelligence entity according to an exemplary embodiment;

FIG. 6 schematically illustrates the steps of the method of FIG. 5 according to an exemplary embodiment;

Figure 1:
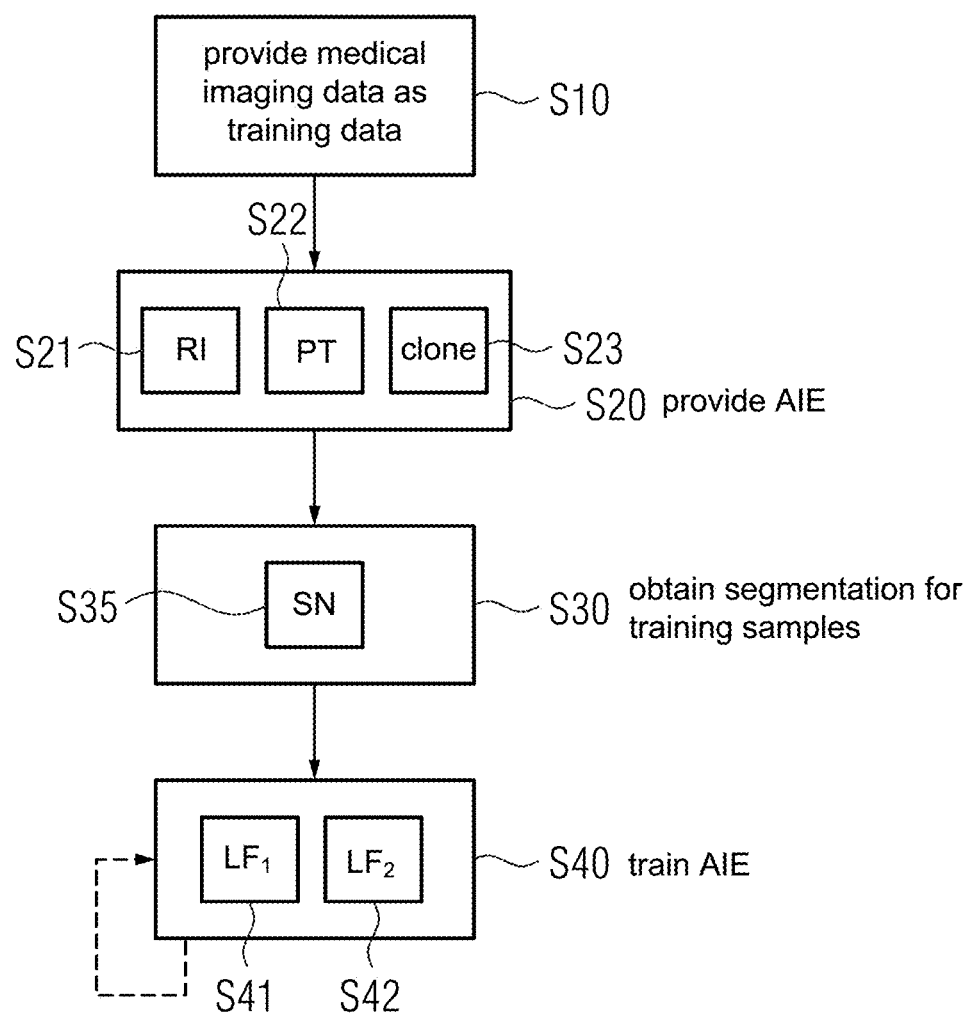

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software. The numbering of method steps is intended to facilitate understanding and should not be construed, unless explicitly stated otherwise, or implicitly clear, to mean that the designated steps have to be performed according to the numbering of their reference signs. In particular, several or even all of the method steps may be performed simultaneously, in an overlapping way or sequentially.

According to a first aspect of the present disclosure, a computer-implemented method for training an artificial intelligence entity, AIE, for detecting abnormalities in medical imaging data of a human organ, in particular a prostate, is provided. In an exemplary embodiment, the method comprising the steps of: providing medical imaging data of the human organ as training data comprising training samples, the medical imaging data comprising a plurality of imaging results from different types of imaging techniques for each training sample of the training data; providing at least one pre-trained or randomly initialized artificial intelligence entity, AIE; and training the AIE using the provided training samples; wherein in a first sub-step, for at least one training sample, a first loss function for at least a sub-structure of the AIE is calculated independently of at least one first spatial region of the human organ; wherein in a second sub-step, for at least one training sample, a second loss function for at least a sub-structure of the AIE is calculated independently of at least one second spatial region of the human organ; and wherein the AIE is trained using at least the calculated first loss function and the calculated second loss function.

Alternatively or additionally, the first loss function is calculated dependent on only the second spatial region and the second loss function is calculated dependent on only the first spatial region.

In an exemplary embodiment, the first loss function is calculated independently of the first spatial region and is further calculated only dependent on the second spatial region, and the second loss function is calculated independently of the second spatial region and is further calculated only dependent on the first spatial region.

Calculating a loss function independently of a spatial region may in particular be understood to mean that no change in any pixel/voxel corresponding to (or, in other words, within) the spatial region within the medical imaging data has any influence on the loss function. Correspondingly, if/when the training is then performed based on such a loss function alone, no change in a pixel/voxel corresponding to the spatial region makes a difference for the gradient descent.

The sub-structures trained in the first and the second sub-steps may be different or may be the same sub-structure. When a single artificial intelligence entity, AIE, is provided, both sub-structures may be identical to this AIE. When more than one AIE is provided, then each sub-structure may refer to a different one of the provided AIEs.

In an exemplary embodiment of the present disclosure, zonal information is used in abnormality detection to make an artificial intelligence entity, AIE, emphasize particular modalities (i.e. particular medical imaging techniques such as particular MRI series) when identifying lesions in particular zones. In the present context, a lesion shall in particular be understood to be a region in an organ or tissue which has suffered damage through injury or disease, such as a wound, ulcer, abscess, or tumor.

This is particularly advantageous for detecting and distinguishing malignant or benign lesions with a distinct feature appearance mainly in one of multiple imaging techniques, for example benign prostatic hyperplasia which mainly effects the transition zone, TZ of the prostate but not the peripheral zone, PZ. Incorporating zonal information can thus significantly reduce false positive detections and thus eliminate unnecessary biopsies.

The aspects of the present disclosure are presented herein with the human prostate as an example. It shall be understood, however, that the same method may also be applied to other organs (e.g., brain, heart, liver, kidney, or the like), either of humans or other organisms, as will become apparent. Therefore, whenever the human prostate is mentioned herein, it shall be understood that this mention be replaced by any other suitable organ according to the principles set out explicitly and/or implicitly herein.

As main examples for different regions within the human prostate which respond differently to different medical imaging scans, the peripheral zone, PZ, and the transition zone, TZ, are chosen. It shall be understood that the described methods and apparatuses can also be applied if the organ is virtually separated into more than two different regions. For example, for most applications it is sufficient if the central zone. CZ, of the prostate is grouped together with the transition zone, TZ, and this approach will be used herein. However, for other applications it may be more suitable to individually distinguish also the central zone, CZ, of the prostate.

In the event that more than two different spatial zones are defined/present, there may be provided one loss function per different spatial zone, and each loss function may be calculated as dependent on only one of the zones and thus independently of all of the other zones. For example, with spatial regions A, B, and C, then the first loss function may be calculated as dependent only on spatial region B and independently of regions A and C; the second loss function may be calculated as dependent only on spatial region C and independently of regions A and B; and the third loss function may be calculated as dependent only on spatial region A and independently of regions B and C.

In an exemplary embodiment, the methods according to the disclosure adopt additional information from the specific anatomical zones, and in many particularly advantageous embodiments also further additional information from the relationship between the specific anatomical zones and medical imaging techniques, much in the same way as experienced physicians do.

Whenever different medical imaging techniques are recited herein, this may refer to different modalities such as computed tomography, CT, magnetic resonance imaging, MRI, X-ray imaging, ultrasound imaging and so on, and/or to specific sub-types or "series" of these modalities, such as differently weighted MR imaging scans. In particular the latter will be mainly used as examples, and among these mainly the T2-weighted MR imaging ("T2W") and the diffusion-weighted MR imaging ("DWI"). The ideas and principles described are, however, equally applicable to other modalities and/or other sub-types, depending on the organ to be scanned, on the personal situation of the patient, on the equipment of a particular medical site and so on.

Results of imaging techniques in particular comprise spatially resolved images, for example bitmaps of pixels or voxels in which each pixel or voxel has a value that indicates a result of a particular imaging technique in a particular position of the human organ.

An artificial intelligence entity, AIE, may in particular be an artificial neural network, ANN, or a pipeline of artificial neural networks and/or other algorithms. Training in this context in particular may comprise updating parameters (for example, weights and biases within an ANN) in order to optimize (usually minimize) a loss (or: cost) function.

Whenever herein "at least a sub-structure" is recited, this may comprise the case that a true sub-structure is meant (i.e. a smaller part of the artificial intelligence entity, AIE, as a whole); the case that the whole artificial intelligence entity, AIE, is meant (in the same sense in that "at least part of" includes also the possibility of "all"); and also the case that more than one sub-structure is meant, i.e. two or more sub-substructures. Examples will be provided, in particular with respect to the drawings, to illustrate at least some of these cases.

The term "sub-step" is used herein for better explaining individual aspects of the method; the distinction into sub-steps may in some instances be a virtual distinction between simultaneous processes for easier explanation. Some sub-steps may be performed simultaneously, other sub-steps may be performed sequentially.

In some advantageous embodiments, refinements, or variants of embodiments, the first spatial region and the second spatial region are disjunct. Thus, there is no spatial region from which both of the first and second loss function are independent.

In some advantageous embodiments, refinements, or variants of embodiments, the first loss function is based only on pixels or voxels of the provided medical imaging data within the second spatial region and/or the second loss function is based only on pixels or voxels of the provided medical imaging data within the first spatial region. This increases the relationship between the respective loss function and a corresponding zone of the human organ. For example, for the case of the human prostate, it is preferred if the first loss function depends only on (i.e. is calculated only based on) pixels or voxels from the peripheral zone, PZ, and that the second loss function depends only on (i.e. is calculated only based on) pixels or voxels from the transition zone, TZ.

In some advantageous embodiments, refinements, or variants of embodiments, the first loss function is calculated independently of the imaging results from at least one first of the types of imaging techniques, and the second loss function is calculated independently of the imaging results from at least one second of the types of imaging techniques. Preferably, each loss function is calculated independently of all but one type of imaging technique, or, in other words, based on only one type of imaging technique of all of the types of imaging techniques for which results are provided in the training samples. This further strengthens the relationship between the respective loss function and a specific imaging technique. For example, for the case of the human prostate, it is preferred if the first loss function depends only (i.e. is only calculated based on) T2W scans, so that the first loss function is particularly associated with the transition zone, TZ, and that the second loss function depends only (i.e. is only calculated based on) DWI scans so that the second loss function is particularly associated with the peripheral zone, PZ.

Then, more preferably, the first loss function is calculated independently of at least one first spatial region of the human organ and also independently from at least one first of the types of imaging techniques, and the second loss function is calculated independently of at least one second spatial region of the human organ and also independently from at least one second of the types of imaging techniques. More preferably, each loss function is calculated based on only a single type of imaging technique and only based on a single spatial region (or: zone) of the human organ. This further strengthens the relationship between the respective loss function, a specific spatial region of the human organ, and a particular imaging technique which is particularly useful ("dominant") for the corresponding spatial region.

For example, for the case of the human prostate, it is preferred if the first loss function depends only on (i.e. is calculated only based on) pixels or voxels from the peripheral zone, PZ, and only on results of (one or more) DWI scans and/or that the second loss function depends only on (i.e. is calculated only based on) pixels or voxels from the transition zone, TZ and only on results of a T2W scan. In this way, the known strong relationships between the zones and the medical imaging techniques are exploited in order to provide the best analysis. In this example, the peripheral zone, PZ, would be defined as the "second spatial region" and the transition zone, TZ, would be defined as the "first spatial region".

In some advantageous embodiments, refinements, or variants of embodiments, in the first sub-step and in the second sub-step the first loss function and the second loss function are calculated for the same at least sub-structure of the AIE, in particular for the same artificial neural network, ANN. Most preferably, the artificial intelligence entity, AIE, consists of this artificial neural network, ANN, which is trained using (at least) both the first and the second loss function. First and second loss function, and optionally one or more additional loss functions, may be combined in a weighted sum to form a total loss function used in a back-propagation algorithm for training the artificial neural network, ANN. The weights of the weighted sum may be suitably chosen hyperparameters. The first and the second loss function can thus also be designated as first and second "loss terms," respectively.

In some advantageous embodiments, refinements, or variants of embodiments, for the first sub-step the imaging results from the at least one first type of imaging technique within each training sample of the at least one training sample are replaced by a pre-defined blank before being used for calculating the first loss function (or: first loss term), and for the second sub-step the imaging results from the at least one second type of imaging technique within each training sample of the same at least one training sample are replaced by the pre-defined blank before being used for calculating the second loss function (or: second loss term).

Using these blanks means that the information from a specific imaging technique is left out from a specific training sample, so that any loss function that is calculated based on an output which results from a training sample thus processed is independent of that specific imaging technique. Similarly, if the blank is applied to all but one results of different imaging techniques, then the loss function calculated based on an output which results from a thus processed training sample depends only on the single remaining imaging technique.

The pre-defined blank may depend on the format of the results of the imaging techniques and may, for example, consist of a vector, matrix or tensor with all "0", all "1", all "0.5" or the like.

In some advantageous embodiments, refinements, or variants of embodiments, in a third sub-step, a third loss function is calculated for each training sample of the same at least one training sample. In the third sub-step each training sample is left unaltered before being used for calculating the third loss function. In other words, each training sample is used "unaltered", i.e. as it is provided—in contrast to the first and second sub-step in this context, which may each make use of training samples that have been processed by replacing parts of the results with a pre-defined blank. The third loss function penalizes differences between the output of the at least sub-structure of the AIE and corresponding labels for each training sample, wherein for the training the labels preferably are ground truth labels provided by a physician annotating the results of the different imaging techniques as a whole for each training sample. The at least sub-structure of the AIE is then trained using a total loss function which is based on at least the first loss function, the second loss function and the third loss function. In particular, the total loss function may be a weighted sum of the first, second, and third loss functions, wherein the weight accorded to each loss function is a hyperparameter.

In some advantageous embodiments, refinements, or variants of embodiments, the training sample with the imaging results from the at least one first type of medical imaging technique replaced by the pre-defined blank is input into the at least sub-structure of the AIE in order to produce a first intermediate spatial feature map. The training sample with the medical imaging results from the at least one second type of medical imaging technique replaced by the pre-defined blank is input into the at least sub-structure of the AIE in order to produce a second intermediate spatial feature map. The unaltered training sample is input into the at least sub-structure of the AIE in order to produce a third intermediate spatial feature map. The intermediate spatial feature maps may be the direct product of the at least sub-structure of the AIE. Alternatively, the intermediate spatial feature maps may be the result of one or more further processing steps on these direct products, respectively. For example, a respective mask may be applied to the respective direct products.

In the present context, a spatial feature map may be understood to refer in particular to a feature map in which each feature indicates a property of a spatial location in the organ, and which comprises information about different spatial locations in the organ. For example, the spatial feature map may comprise a feature for each pixel or voxel of medical imaging data.

In an exemplary embodiment, the first loss function penalizes differences between the third intermediate spatial feature map and the first intermediate spatial feature map, and the second loss function penalizes differences between the third intermediate spatial feature map and the second intermediate spatial feature map. In this way, the first and the second loss function push the at least sub-structure being trained towards a specific combination of spatial region of the human organ on the one hand, and medical imaging technique on the other hand.

In some advantageous embodiments, refinements, or variants of embodiments, the method comprises a step of pre-training at least a sub-structure of the artificial intelligence entity, AIE (or even the AIE as a whole). Pre-training may, for example, be performed using a set of labelled training data showing not only the organ of interest (e.g. the prostate) but showing a plurality of different organs with corresponding abnormality heat map labels so as to increase the number of training samples. Using pre-trained artificial intelligence entities, in particular pre-trained artificial neural networks, ANN, is an effective way to improve the starting performance of an artificial intelligence entity, AIE, to be trained.

In some advantageous embodiments, refinements, or variants of embodiments, the first sub-step comprises training a first copy (or: clone, or: instance) of the pre-trained sub-structure using the first loss function in order to obtain a first trained sub-structure. Moreover, the second sub-step comprises training a second copy (or: clone, or: instance) of the pre-trained sub-structure using the second loss function in order to obtain a second trained sub-structure. In other words, a common starting point, namely the pre-trained sub-structure, is provided, two copies of it are provided (or one original and one copy, to be precise), and the two copies are then separately trained using different loss functions.

Again, each loss function is independent of a certain spatial region (e.g. zone of the prostate), and preferably only depends on one specific spatial region. This may be achieved, for example, by using a spatial mask on both the ground truth label and the output of the sub-structure being trained, wherein the spatial mask comprises values of "1" for all pixels or voxels of the spatial region on which the loss function shall depend and further comprises values of "0" for all other pixels or voxels, specifically the pixels or voxels of the other spatial regions.

It shall be understood that, if more than two specific spatial regions with different properties and/or different responses to different medical imaging techniques are present with the human organ of interest, correspondingly more copies of the pre-trained sub-structure may be provided. Each of these copies is then trained separately with a corresponding loss function, wherein each loss function only depends on one of the spatial regions and is independent on the other spatial regions. For each spatial region a corresponding spatial mask may be provided.

In these embodiments, then (fine-tuned) trained sub-structures are provided by the method, each sub-structure fine-tuned to one specific spatial region of the human organ of interest. For the production mode (or: inference stage), then input samples can be provided to each of these sub-structures separately, and a total abnormality heat map may be generated by taking from each trained sub-structure the information about the spatial region for which it is fine-tuned, i.e. to which it corresponds (or: with which it is associated).

The disclosure also provides, according to a second aspect, a method for detecting abnormalities in medical imaging data of a human organ, in particular a prostate. In an exemplary embodiment, the method includes: providing the first trained sub-structure and the second trained sub-structure, in particular according to any embodiment of the first aspect of the present disclosure; inputting a data sample (or: input sample) comprising a plurality of imaging results for the human organ from different types of imaging techniques into the first trained sub-structure in order to generate a first intermediate spatial feature map; inputting the same data sample into the second trained sub-structure in order to generate a second intermediate spatial feature map; and generating an abnormality heat map (or: total abnormality heat map) based on the generated first intermediate spatial feature map and the generated second intermediate spatial feature map.

In an exemplary embodiment, the abnormality heat map is generated by taking pixels or voxels for the second spatial region from the first intermediate spatial feature map and by taking pixels or voxels for the first spatial region from the second intermediate spatial feature map such that the abnormality heat map comprises pixels or voxels for the first and the second spatial region. Correspondingly, for N>2 two spatial regions to be distinguished, N (fine-tuned) trained sub-structures may be provided, each associated with a specific spatial region, and the (total) abnormality heat map is then generated by taking from each intermediate spatial feature map the pixels or voxels belonging to that associated specific spatial region only. In this way, it is ensured that every pixel or voxel of the input data sample is analyzed by a fine-tuned sub-structure trained specifically for the spatial region to which the pixel or voxel belong.

In some advantageous embodiments, refinements, or variants of embodiments, a segmentation (e.g. comprising, or consisting of, one or more segmentation masks represented by a corresponding segmentation mask channel) is provided for identifying at least the first spatial region and the second spatial region within the input data sample, and wherein the pixels or voxels are taken from the first intermediate spatial feature map and the second intermediate spatial feature map, respectively, based on the segmentation. The segmentation may be automatically provided by inputting the data sample into a trained artificial intelligence segmentation entity (e.g. a segmentation artificial neural network). Alternatively, the data sample may already comprise a segmentation, e.g. one or more segmentation mask (or: segmentation mask channels).

According to a third aspect, the disclosure provides a system for detecting abnormalities in medical imaging data of a human organ, in particular a prostate. In an exemplary embodiment, the system includes: an input interface for receiving a data sample comprising a plurality of imaging results for the human organ from different types of imaging techniques; a computing device configured to implement a trained artificial intelligence entity, AIE, (in particular a trained artificial neural network, ANN), comprising a first trained sub-structure, a second trained sub-structure, and a fusion module; wherein the first trained sub-structure is configured and trained to receive the data sample from the input interface and to provide, as its output based thereon, a first intermediate spatial feature map; wherein the second trained sub-structure is configured and trained to receive the data sample from the input interface and to provide, as its output based thereon, a second intermediate spatial feature map; wherein the fusion module is configured to generate an abnormality heat map by taking pixels or voxels for the second spatial region from the first intermediate spatial feature map and by taking pixels or voxels for the first spatial region from the second intermediate spatial feature map such that the abnormality heat map comprises pixels or voxels for the first and the second spatial region; and an output interface for outputting at least the generated abnormality heat map.

The first and second trained sub-structure may be trained according to any embodiment of the method of the second aspect of the present disclosure.

The input interface and/or the output interface may be realized in hardware and/or software. The input interface and/or the output interface can each comprise one or more different communication channels using one or more different communication protocols (e.g. HTTP). Each of the input interface and/or the output interface can be configured to connect to a cable-bound data connection and/or to a wireless data connection such as Bluetooth, Zigbee, WiFi and so on. The input interface and/or the output interface may also be configured to connect to Ethernet networks.

The computing device may be realized as any device, or any means, for computing. For example, the computing device may comprise at least one data processing (or: calculating) unit such as at least one central processing unit, CPU, and/or at least one graphics processing unit, GPU, and/or at least one field-programmable gate array, FPGA, and/or at least one application-specific integrated circuit, ASIC, and/or any combination of the foregoing. The computing device may comprise a working memory operatively coupled to the at least one processing unit and/or a non-transitory memory operatively connected to the at least one processing unit and/or the working memory.

The computing device may be partially or completely realized as a remote device, for example as a cloud computing platform.

In some advantageous embodiments, variants, or refinements of embodiments, the computing device is further configured to implement a trained artificial intelligence segmentation entity configured and trained for receiving the data sample as its input and to output a segmentation as its output based thereon, and wherein the fusion module is configured to take the pixels or voxels based on the segmentation for the generating of the abnormality heat map.

According to a fourth aspect, the disclosure provides a system for detecting abnormalities in medical imaging data of a human organ, in particular a prostate. In an exemplary embodiment, the system includes: an input interface for receiving a data sample comprising a plurality of imaging results for the human organ from different types of imaging techniques; a computing device configured to implement an artificial intelligence entity, AIE, trained according to a method according to any embodiment of the first aspect of the present disclosure, wherein the trained AIE, preferably a trained artificial neural network, is configured and trained to receive the data sample from the input interface and to provide, as its output based thereon, an abnormality heat map; and an output interface for outputting at least the generated abnormality heat map.

According to a fifth aspect, the disclosure also provides a use of an artificial intelligence entity. AIE, trained according to a method according to any embodiment of the first aspect of the present disclosure, for detecting abnormalities in medical imaging data of a human organ, in particular a prostate. In an exemplary embodiment, the trained AIE is a trained artificial neural network ANN. In an exemplary embodiment, the use of the trained AIE, particularly trained ANN, is in a method according to any embodiment of the second aspect of the disclosure.

According to a sixth aspect, the disclosure also provides a use of an artificial intelligence entity, AIE, trained according to a method according to any embodiment of the first aspect of the present disclosure, in a system for detecting abnormalities in medical imaging data of a human organ, in particular a prostate. In an exemplary embodiment, the trained AIE is a trained artificial neural network ANN. The system is preferably a system according to any embodiment of the third or fourth aspect.

According to a seventh aspect of the present disclosure, a computer program product is provided comprising executable program code configured to, when executed by a computing device, to perform the method according to any embodiment of the first aspect of the present disclosure and/or according to any embodiment of the second aspect of the present disclosure.

According to an eighth aspect of the present disclosure, a non-transitory, computer-readable data storage medium is provided, which comprises program code configured to, when executed by a computing device, executes the method according to an embodiment of the first aspect of the present disclosure and/or according to any embodiment of the second aspect of the present disclosure. Such a data storage medium may be, for example, a USB stick, a CD ROM, a DVD ROM, a Blue-Ray Disc, a hard drive, a solid state drive and/or the like.

According to a ninth aspect of the present disclosure, a data stream is provided, which comprises program code (or which is configured to generate program code), configured to, when executed by a computing device, perform the method according to any embodiment of the first aspect of the present disclosure and/or according to any embodiment of the second aspect of the present disclosure. The data stream may, for example, be provided by a server and be downloaded by a client or a user terminal or by a personal computer or a laptop.

Additional advantageous variants, refinements, embodiments and aspects of the disclosure will become more obvious in connection with the following description with reference to the drawings.

It will be understood that specific features, options or variants as are described with respect to specific aspects of the present disclosure may be equally, similarly or analogously also be implement in embodiments according to other aspects of the present disclosure.

FIG. 1 is a schematic flow diagram illustrating a method for training an artificial intelligence entity, AIE, for detecting abnormalities in medical imaging data of a human organ, in particular a human prostate. The general concepts will be described with respect to the human prostate and with respect to its peripheral zone, PZ, and its transition zone, TZ, but it will be apparent that these concepts are not in any way limited to this particular application and can be readily applied to numerous other organs and/or zones thereof. The method is in particular applicable to organs with distinct and disjunct zones (or: regions) which respond differently to (or: are scanned differently by) different medical imaging techniques.

Figure 2:
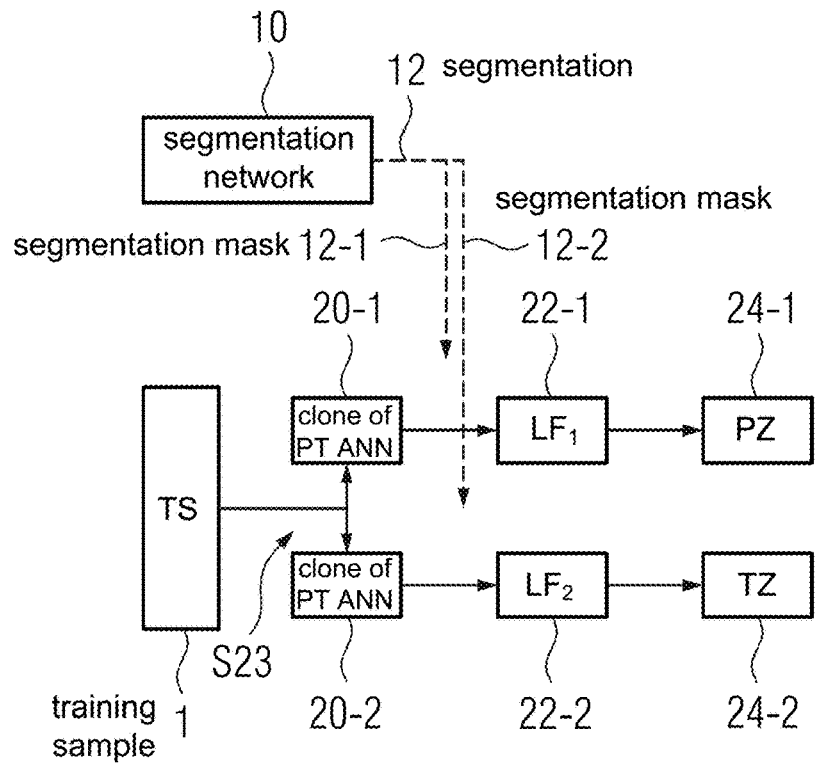

FIG. 2 schematically illustrates the steps of the method of FIG. 1.

The method according to FIG. 1 provides an artificial intelligence entity, AIE, in particular artificial neural network, ANN, which essentially and effectively mimics the decision-making procedure of a trained radiologist. The main idea is to add additional inputs from the T2W scans for the information within the transition zone, TZ, and to add additional inputs from the DWI scans for the information within the peripheral zone, PZ.

In a step S10, medical imaging data of the human organ, in particular the prostate, are provided as training data. The training data is organized in training samples, wherein each training sample comprises a plurality of imaging results from different types of imaging techniques. These imaging results all show the same organ, i.e. they all comprise pixels or voxels that relate to spatial positions of the organ. The training samples are also provided with labels as ground truths for the training, i.e. with additional information, preferably for each pixels or voxels, about which result of the artificial intelligence entity, AIE, is to be achieved.

In the examples described herein, the result is usually an abnormality heat map, although other possible results will be readily appreciated by the skilled person. The heat map can be a feature map of entries, wherein each entry corresponds to one pixel of the sample used as input. The entries may for example be binary, e.g. 0—no abnormality likely or 1—abnormality likely, or percentile, e.g. 0—abnormality highly unlikely, 0.5—equal chances of abnormality or no abnormality, 1—abnormality highly likely. In the latter case, the heat map may also be designated as a probability heat map, since its entries indicate a probability for each pixels or voxels to belong to a particular abnormality, e.g. a cancerous growth or lesion. Other types of heat maps may also be envisaged.

Thus, in the case of an abnormality heat map, the training samples are provided with labels for each pixels or voxels which indicates the desired entry of the heat map. During training, the parameters of the artificial intelligence entity, AIE, or at least sub-structures or parts of it, will be adjusted so as to minimize the losses resulting from differences between the actually output abnormality heat map and the abnormality heat map according to the provided labels.

The label abnormality heat maps are provided, for example, by trained physicians which review the medical imaging results comprised in each training sample and mark which pixels, according to their expertise, belong to abnormalities and which do not.

As has been described in detail, various results from various imaging techniques may be used to form the training samples (and will, accordingly, also be used as input during the production, or inference, phase of the artificial intelligence entity, AIE).

Since the present examples focus mostly on the human prostate, training samples comprising results of a T2W imaging scan and further comprising results of a DWI scan will now be discussed for the sake of simplicity, although it shall be understood that training samples may include any other types of imaging scan results as well, in particular for other organs. It shall also be understood that DWI here may signify different sub-types of DWI scans, for example a DWI/ADC sequence or a DWI High B sequence.

In a step S20, a pre-trained or randomly initialized artificial intelligence entity, AIE, is provided. In particular, the artificial intelligence entity, AIE, may comprise, or consist of, an artificial neural network, ANN, in particular a deep artificial neural network, DNN. It will be apparent to the skilled person that different types of artificial neural networks, ANN, in particular DNNs, may be employed as or within the artificial intelligence entity, AIE, in particular a U-net, a U-net with Res-Net blocks or any of the other types of artificial neural network, ANN, as described in WO 2019/238804 A1.

The providing S20 of the artificial intelligence entity, AIE, may comprise a sub-step S21 of providing a randomly initialized artificial intelligence entity, AIE (for example an ANN with randomly initialized weights and biases) and pre-training S22 the artificial intelligence entity, AIE, for example using a set of labelled training data showing not only the organ of interest (herein: the prostate) but showing a plurality of different organs with corresponding abnormality heat map labels so as to increase the number of training samples. Providing a pre-trained artificial intelligence entity, AIE, is preferred since this always improves the performance of the artificial intelligence entity, AIE.

In the following, as an example, the case will be described that at least a pre-trained artificial neural network, ANN, is provided.

In a sub-step S23, the provided pre-trained artificial neural network, ANN, is then cloned (i.e. copied once) so that two identical pre-trained artificial neural networks, ANN, are obtained: a first pre-trained artificial neural network, ANN, and a second pre-trained artificial neural network, ANN.

In a step S30, for each of the training samples a segmentation is obtained, i.e. information about which pixels or voxels of the medical imaging scan results belong to which of a plurality of pre-specified regions of the human organ. In the case of the prostate, in particular the transition zone, TZ, and the peripheral zone, PZ, are useful to distinguish from one another, so that the segmentation for each training sample may comprise one or more mask channels indicating which pixels or voxels belong to the peripheral zone, PZ, and which pixels or voxels belong to the transition zone, TZ. Preferably, a first mask channel indicates for each pixel whether it belong to the peripheral zone, PZ, by a corresponding "1" in the channel, or whether it does not belong to the peripheral zone, PZ, by a corresponding "0" in the channel, and a second mask channel indicates for each pixel whether it belong to the transition zone, TZ, by a corresponding "1" in the channel, or whether it does not belong to the transition, TZ, by a corresponding "0" in the channel.

For the training samples, the segmentations may be provided simply as part of the training data, just as the labels are provided. For example, the physician who has classified the pixels or voxels of the medical imaging scan results into pixels or voxels containing abnormalities or no abnormalities may also have provided a segmentation of the same medical imaging scan results into (at least) transition zone, TZ, and peripheral zone, PZ.

As an alternative, in a sub-step S35 of step S30, the medical imaging scan results of the training samples may be input into a segmentation network (i.e. an artificial neural network, ANN, trained for producing the desired segmentation). Advantageously, since usually in the later production (or: inference) phase no segmentation is a priori available in any case, the same segmentation network may also be used then.

In one or more (generally a large number of) first sub-steps S41 of training S40, the first pre-trained artificial neural network, ANN, is then trained to obtain a PZ-specific sub-structure, and in one or more (generally a large number of) second sub-steps S42 of the training S40, the second pre-trained artificial neural network, ANN, is trained to obtain a PZ-specific sub-structure.

For the first sub-step S41, a first loss function is calculated for each training sample, wherein the first loss function only depends on pixels or voxels of the peripheral zone, PZ, according to the segmentation, and is independent from pixels or voxels of the transition zone, TZ. In more abstract words, the calculation S41 of the first loss function is independent of a first spatial region (the transition zone, TZ), and is only dependent on a second spatial region (the peripheral zone, PZ).

This may e.g. be achieved in that only differences between the output of the PZ-specific sub-structure and the ground truth label in the pixels or voxels of the peripheral zone, PZ, are penalized during training. In other words, the first loss function is only changed when any of the pixels or voxels within the peripheral zone, PZ, is changed but remains unchanged for any change in any of the pixels or voxels within the transition zone, TZ.

One simple way to realize this is, for example, to use a mask that gives a 1 for all pixels or voxels of the peripheral zone, PZ. This mask may then be applied automatically to both the output of the PZ-specific sub-structure and to the ground truth for the respective training sample. The first loss function may be designed to penalize pixel-(or voxel-) wise difference between these two heat maps, e.g. using an L2 metric. Now, since all pixels or voxels not of the peripheral zone, PZ, will have a value of zero both in the output of the PZ-specific sub-structure and the ground truth, the difference between them will be zero and there will be no penalization by the first loss function. This also means that when the PZ-specific sub-structure is trained using the first loss function, it will learn specifically to find accurate results for the peripheral zone, PZ, while its results for the transition zone, TZ, will be unsupervised.

The training of the PZ-specific sub-structure is done in the usual way based on the first loss function, i.e. in an iterative process parameters (e.g. weights and biases) of the sub-structure are updated based on a back-propagation algorithm in order to minimize the first loss function. Thus, one iteration of the first sub-step S41 may comprise inputting one or more training samples into the PZ-specific sub-structure, generating an output of the sub-structure based thereon, calculating the first loss function for one or more training samples, and then use a back-propagation algorithm to change parameters of the PZ-specific sub-structure such as to best minimize the first loss function (e.g. gradient descent).

For the second sub-step S42, a second loss function is calculated for each training sample, wherein the second loss function only depends on pixels or voxels of the transition zone, TZ, according to the segmentation, and is independent from pixels or voxels of the peripheral zone. PZ. In other words, the calculation S42 of the second loss function is independent of the second spatial region (the transition zone, TZ), and is only dependent on the first spatial region (the peripheral zone, PZ).

This may e.g. be achieved in that only differences between the output of the TZ-specific sub-structure and the ground truth label in the pixels or voxels of the transition zone, TZ, are penalized during training. In other words, the second loss function is only changed when any of the pixels or voxels within the transition zone, TZ, is changed but remains unchanged for any change in any of the pixels or voxels within the peripheral zone, PZ. This can be realized in the same way as has been described in the foregoing for the first sub-step S41.

As a result of the repeated performing of the first and second sub-steps S41, S42, then a trained PZ-specific sub-structure and a training TZ-specific sub-structure are provided. Each of these sub-structures is fine-tuned for detecting abnormalities within their respective zone and produce less reliable (or even random) results for the pixels or voxels outside of the respective zone.

These sub-structures may then be used individually, or they may be combined in an artificial intelligence entity, AIE, or in a pipeline, to produce even better or more complete results, as will be explained in more detail in the following.

FIG. 2 shows a schematic block diagram illustrating one possible realization of the method of FIG. 1. A training sample 1 (e.g. multi-parametric MRI images) which have been provided in step S10 are input into a segmentation network 10 in order to generate the segmentation 12 for the training sample 1. The segmentation 12 may comprise a first segmentation mask 12-1 with a "1" for each pixels or voxels that belongs to the peripheral zone, PZ, and with a "0" for each pixel or voxel that belongs to the transition zone, TZ, and a second segmentation mask 12-2 with a "1" for each pixel or voxel that belongs to the transition zone, TZ, and with a "0" for each pixel or voxel that belongs to the peripheral zone, PZ.

The training sample 1 is also input into each of two identical copies (clones) 20-1, 20-2 of the same pre-trained artificial neural network, ANN. One copy 20-1 is the starting point for the PZ-specific sub-structure, and one copy 20-2 is the starting point for the TZ-specific sub-structure.

Based on the input training sample 1, each of the sub-structures 20-1, 20-2 produces an output. Using the segmentation 12, for the PZ-specific sub-structure a first loss function 22-1 is calculated which only takes into account pixels or voxels from the peripheral zone, PZ, and which is independent of the pixels or voxels from the transition zone, TZ.

Similarly, using the segmentation 12, for the TZ-specific sub-structure a second loss function 22-2 is calculated which only takes into account pixels or voxels from the transition zone, TZ, and which is independent of the pixels or voxels from the peripheral zone, PZ. As has been described in the foregoing, the training samples 1 are provided with labels (more specifically: label abnormality heat maps), and the first and/or second loss function may be realized as any known loss function for penalizing differences between the values of the label abnormality heat maps for each pixels or voxels and the corresponding output heat map of the sub-structures 20-1, 20-2. For example, binary cross entropy (BCE) loss functions may be used.

By repeated performing of the respective sub-steps S41, S42 then final results for the PZ-specific sub-structure 24-1 and for the TZ-specific sub-structure 24-2 are provided.

Figure 3:
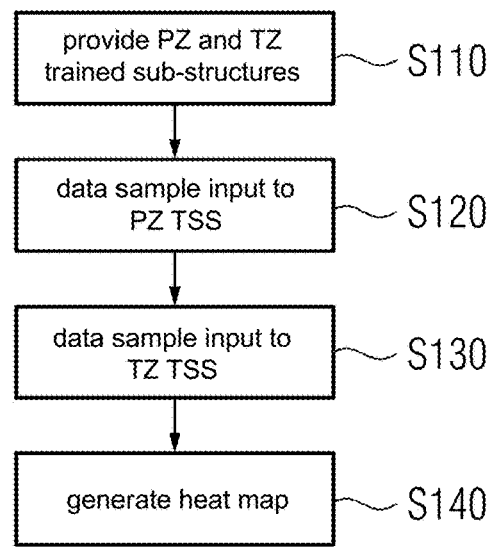
Figure 4:
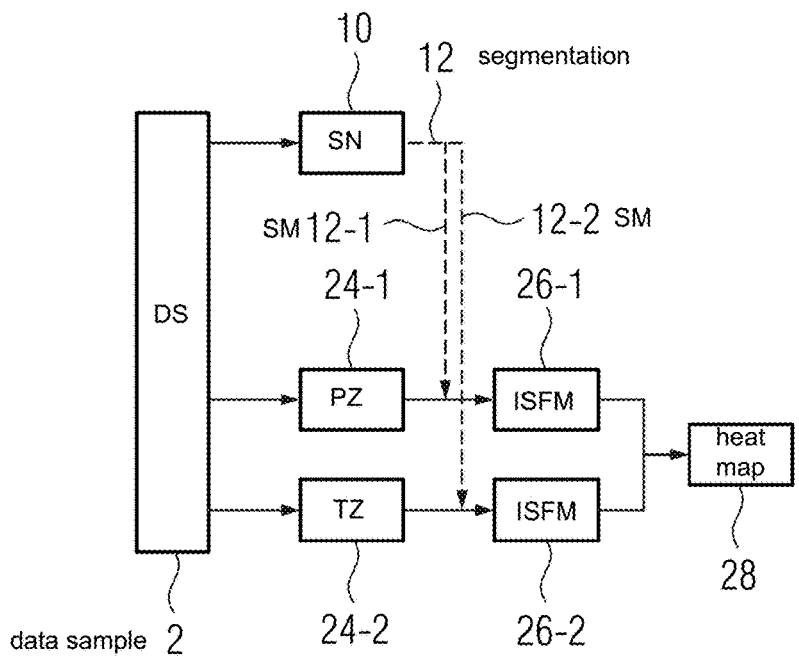

FIG. 3 shows a schematic flow diagram for illustrating a method for detecting abnormalities in medical imaging data of a human organ, in particular of a prostate. FIG. 4 shows a schematic block diagram illustrating one possible realization of the method of FIG. 3. The methods of FIG. 3 and/or FIG. 4 may be seen as realizations of an inference stage (or: production mode) of the artificial intelligence entity, AIE, which has been trained with the method as described with respect to FIG. 1 and/or FIG. 2.

In a step S110, a first and a second trained sub-structure are provided, namely a trained PZ-specific sub-structure 24-1 and a trained TZ-specific sub-structure 24-2, in particular in the way as has been described in the foregoing with respect to FIG. 1 and/or FIG. 2.

In a step S120, a data sample 2 comprising a plurality of imaging results for the human organ (in particular prostate) from different types of imaging techniques, e.g. a real-world multi-parametric MRI image, is input into the trained PZ-specific sub-structure 24-1 in order to generate a first intermediate spatial feature map 26-1 (here specifically: abnormality heat map).

In a step S130, the data sample 2 is input also into the trained TZ-specific sub-structure 24-2 to generate a second intermediate spatial feature map 26-2 (here specifically: abnormality heat map).

In a step S140, a total abnormality heat map 28 is generated based on the first intermediate spatial feature map 26-1 and the second intermediate spatial feature map 26-2, specifically such that the abnormality heat map 28 comprises the pixels or voxels for the peripheral zone, PZ, from the first intermediate spatial feature map 26-1 and the pixels or voxels for the transition zone, TZ, from the second intermediate spatial feature map 26-2. The term "total" here refers to the fact that the total abnormality heat map 28 comprises the best possible results not only for one zone (or: region) of the human organ but for all of its zones.

The total abnormality heat map 28 can, for example, be generated as illustrated with FIG. 4:

The data sample 2 may be input into a segmentation network 10, preferably the same segmentation network 10 that has already been used for providing the PZ-specific sub-structure 24-1 and the TZ-specific sub-structure 24-2. The first segmentation mask 12-1 may be convolved (pixel-wise or voxel-wise multiplied) with the output of the trained PZ-specific sub-structure 24-1 in order to generate a processed first intermediate spatial feature map 26-1, and the second segmentation mask 12-2 be convolved (pixel-wise or voxel-wise multiplied) with the output of the trained TZ-specific sub-structure 24-2 in order to generate a processed second intermediate spatial feature map 26-2. In this way, the thus processed intermediate spatial features maps 26-1, 26-2 each comprise non-zero values only for the pixels or voxels of their respective corresponding zone (or: region) and zero values otherwise.

Then, these processed intermediate spatial feature maps 26-1, 26-2 can simply be added (or: fused) to generate the total abnormality heat map 28. Since in the present example the total abnormality heat map indicates the possibility (binary entries) or likelihood (percentile entries) malignant lesions, it may also be designated as a lesion malignancy map.

Figure 5:
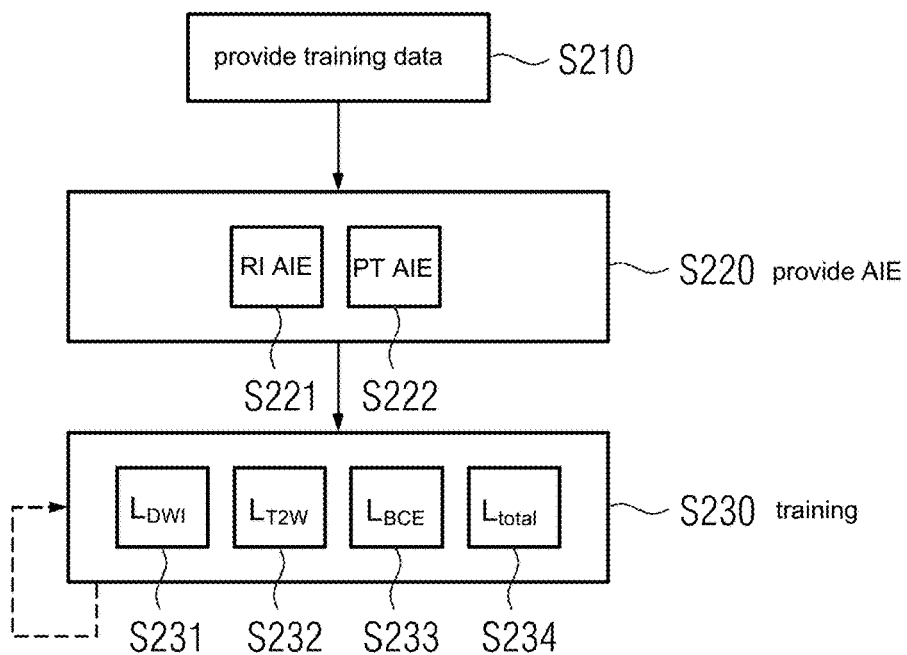

FIG. 5 is a schematic flow diagram illustrating a further method for training an artificial intelligence entity, AIE, for detecting abnormalities in medical imaging data of a human organ, in particular a human prostate. Again, the general concepts will be described with respect to the human prostate and with respect to its peripheral zone, PZ, and its transition zone, TZ, but it will be apparent that these concepts are not in any way limited to this particular application and can be readily applied to numerous other organs and/or zones thereof. The method is in particular applicable to organs with distinct and disjunct zones (or: regions) which respond differently to (or: are scanned differently by) different medical imaging techniques.

Figure 6:
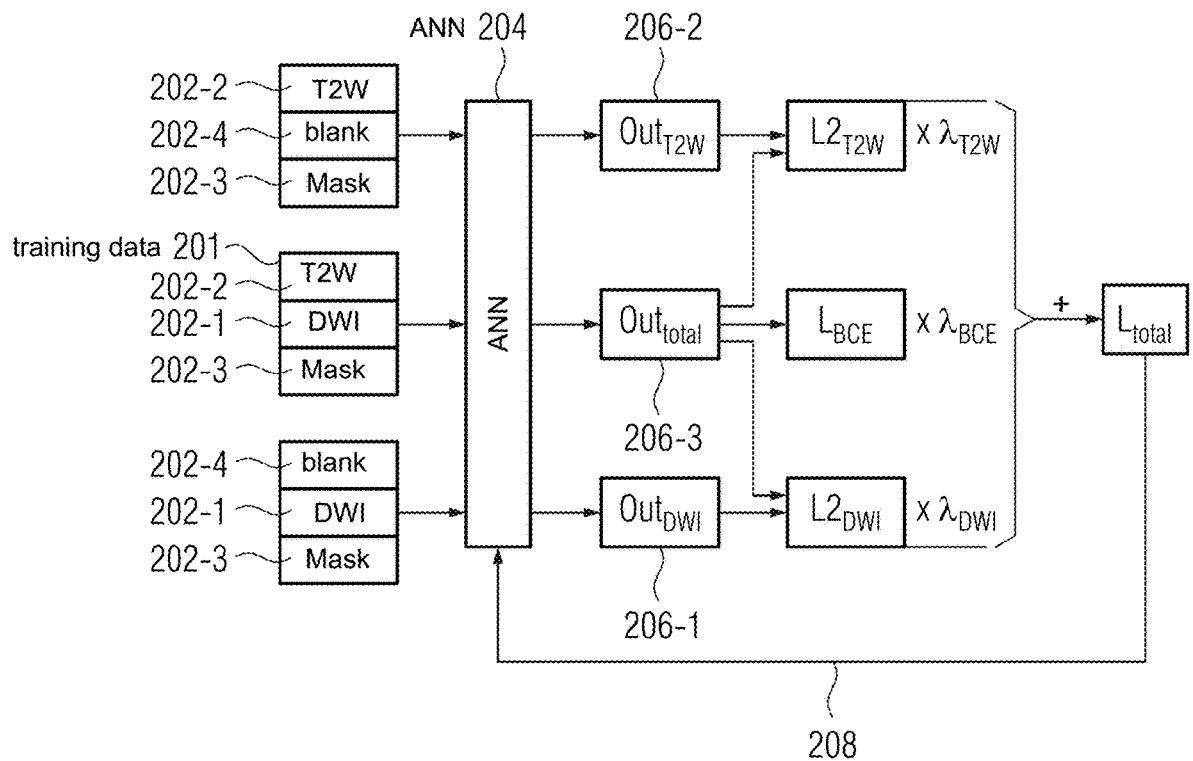

FIG. 6 schematically illustrates the steps of the method of FIG. 5.

The method according to FIG. 5 provides an end-to-end artificial intelligence entity, AIE, in particular end-to-end artificial neural network, ANN, which essentially and effectively mimics the decision-making procedure of a trained radiologist. The main idea is to add additional inputs from the T2W scans for the information within the transition zone, TZ, and to add additional inputs from the DWI scans for the information within the peripheral zone, PZ.

In a step S210, medical imaging data of the human organ, in particular the prostate, are provided as training data 201, as illustrated in FIG. 6. The training data 201 is organized in training samples, wherein each training sample comprises a plurality of imaging results 202-1, 202-2 from different types of imaging techniques. In FIG. 6, again for the example of the human prostate, the training data 201 comprises first imaging results 202-1 from DWI scans, and second imaging results 202-2 from T2W scans.

The training data 201 also comprise, in this example, at least one mask channel 202-3 which provides segmentation information, i.e. information about which pixels or voxels belong to the transition zone, TZ, or to the peripheral zone, PZ, respectively. In some variants, as has been described in the foregoing, the at least one mask channel may be automatically generated based on the other channels with the imaging results 202-1, 202-2 in a foregoing method step, in particular using a segmentation network 10 as has been described in the foregoing.

Preferably, a first mask channel indicates for each pixel whether it belong to the peripheral zone, PZ, by a corresponding "1" in the channel, or whether it does not belong to the peripheral zone, PZ, by a corresponding "0" in the channel, and a second mask channel indicates for each pixel whether it belong to the transition zone, TZ, by a corresponding "1" in the channel, or whether it does not belong to the transition, TZ, by a corresponding "0" in the channel.

The training data 201 are also provided with labels in form of a label abnormality heat map for each of the training samples as has been described in the foregoing with respect to FIG. 1 and FIG. 2.

In a step S220, a pre-trained or randomly initialized artificial intelligence entity, AIE, is provided. In particular, the artificial intelligence entity, AIE, may comprise, or consist of, an artificial neural network, ANN, in particular a deep artificial neural network, DNN. It will be apparent to the skilled person that different types of artificial neural networks, ANN, in particular DNNs, may be employed as or within the artificial intelligence entity, AIE, in particular a U-net, a U-net with Res-Net blocks or any of the other types of artificial neural network, ANN, e.g. as described in WO 2019/238804 A1.

The providing S220 of the artificial intelligence entity, AIE, may comprise a sub-step S221 of providing a randomly initialized artificial intelligence entity, AIE (for example an ANN with randomly initialized weights and biases) and pre-training S222 the artificial intelligence entity, AIE, for example using a set of labelled training data showing not only the organ of interest (herein: the prostate) but showing a plurality of different organs with corresponding abnormality heat map labels so as to increase the number of training samples. Providing a pre-trained artificial intelligence entity, AIE, is preferred since this always improves the performance of the artificial intelligence entity, AIE.

In the following, as an example, the case will be described that at least a pre-trained artificial neural network, ANN 204, is provided.

Then, during training S230, this provided pre-trained artificial neural network, ANN 204, is further trained with the provided training data 201 using a total loss function $L_{total}$ which comprises, or consists of, three separate loss function terms that are added, preferably using a weighted sum:

$$L_{total} = \lambda_{BCE} * L_{BCE} + \lambda_{DWT} * L_{DWT} + \lambda_{T2W} * L_{T2W} \quad (1)$$

These terms will be explained in detail in the following.

Referring to FIG. 6, three separate outputs are produced with the same ANN 204 in the same training state (i.e. with the same current set of parameters, e.g. weights and biases), based on three different inputs:

a first output 206-1 (or intermediate spatial feature map) is generated by the ANN 204 as a result of inputting a training sample of the training data 201, wherein the first imaging results, from the DWI scan (DWI channel), have been replaced by a blank 202-4;

a second output 206-2 (or intermediate spatial feature map) is generated by the ANN 204 as a result of inputting the same training sample of the training data 201, wherein the second imaging results, from the T2W scan (T2W channel), have been replaced by a blank 202-4; and a third output 206-3 (or intermediate spatial feature map) is generated by the ANN 204 as a result of inputting the same training sample of the training data 201, without any previous alterations.

A "blank" 202-4 may herein be a channel of the same spatial dimension as the imaging result channels but with all of its pixels or voxels set to the same value, e.g. to "0", to "1", to "0.5" or so, depending on the specific realization and the values used in the imaging results.

As a result, the first output 206-1 will in principle be more suitable for detecting abnormalities in the peripheral zone, PZ, as it contains, apart from the—for this region dominant—first imaging results 202-1 from the DWI scan less "noise", i.e. less (or none at all) non-dominant imaging results. Similarly, the second output 206-2 will in principle be more suitable for detecting abnormalities in the transition zone, TZ, as it contains, apart from the—for this region dominant—second imaging results 202-2 from the T2W scan less "noise", i.e. less (or none at all) non-dominant imaging results. Finally, the third output 206-3 will be balanced, taking all of the imaging results 202-1, 202-2 into account.

These outputs 206-1, 206-2, 206-3 are then used to calculate S234 the total loss function $L_{total}$ in order to improve, via back-propagation 208, the parameters of the ANN 204 in an iterative process.

Returning to the formula (1) above for the total loss function $L_{total}$, the term $L_{BCE}$, multiplied with a weighting factor $\lambda_{BCE}$ as one hyperparameter, is a binary cross entropy term which simply penalizes, in the usual way, the difference (or: loss) between the ground truth according to the labels of the training data 201 and the third output 206-3, preferably pixel-wise (or voxel-wise, when the medical imaging results 202-1, 202-2 are provided as voxels instead of pixels, or when in a pre-processing steps pixels are transformed into voxels or the like). $L_{BCE}$ is calculated in a sub-step S233.

Moving on to the next term, the symbol $L_{DWT}$ symbolizes a first loss function which penalizes differences (again, preferably pixel- or voxel-wise) between the first output 206-1 and the third output 206-3 but only as far as the peripheral zone, PZ, is concerned. In other words, the first loss function is independent of any pixels or voxels within the transition zone, TZ (or, for that matter, in any other region of the prostate).

Thus, $L_{DWT}$ may be calculated S231 as follows, with the first output 206-1 designated as $Out_{DWT}$ and with the third output 206-3 designated as $Out_{total}$:

$$L_{DWT} = \|y_{PZ} * (Out_{total} - Out_{DWT})\|^2$$

with the L2-norm $\|\cdot\|^2$, with * here a elementwise (i.e. pixel-wise) product, and with $y_{PZ}$ a mask (first mask channel) having 1's for pixels or voxels that belong to the peripheral zone, PZ, and with 0's for pixels or voxels that do not belong to the peripheral zone, PZ, or which in particular belong to the transition zone, TZ. As in the case of $\lambda_{BCE}$, $\lambda_{PWT}$ is a hyperparameter giving a relative weight to the first loss function within the total loss function $L_{total}$.

Again moving on to the next term, the symbol $L_{T2W}$ symbolizes a second loss function which penalizes differences (again, preferably pixel- or voxel-wise) between the second output 206-2 and the third output 206-3 but only as far as the transition zone, TZ, is concerned. In other words, the second loss function is independent of any pixels or voxels within the peripheral zone, PZ (or, for that matter, in any other region of the prostate).

Thus, $L_{T2W}$ may be calculated S232 as follows, with the second output 206-2 designated as $Out_{T2W}$ and with the other symbols as defined above:

$$L_{T2W} = \|y_{TZ} * (Out_{total} - Out_{T2W})\|^2,$$

with $y_{TZ}$ a mask (second mask channel) having 1's for pixels or voxels that belong to the transition zone, TZ, and with 0's for pixels or voxels that do not belong to the transition zone, TZ, or which in particular belong to the peripheral zone, PZ.

As in the case of $\lambda_{BCE}$, $\Delta_{T2W}$ is a hyperparameter giving a relative weight to the second loss function within the total loss function $L_{total}$.

Advantageously, the first and second mask channels ($y_{PZ}$ and $y_{TZ}$) are not only used for the calculation of the respective loss functions but also as further input into the ANN 204 besides the medical imaging data themselves.

In some variants, $\lambda_{T2W}$ is equal to $\lambda_{DWI}$, and it is preferred that $\lambda_{BCE} \geq 2\lambda_{DWI}$, more preferably $\lambda_{BCE} \geq 3\lambda_{DWI}$, still more preferably $\lambda_{BCE} \geq 4\lambda_{DWI}$. However, the hyperparameters $\lambda_{T2W}$, $\lambda_{BCE}$ and $\lambda_{DWI}$ may also be the result of a grid search to find optimal hyperparameters on a training dataset.

Again, the described is a specific example for the case of the human prostate and for the case of exactly two zones of the prostate and for exactly two medical imaging scans, T2W and DWI. The principle is easily applied to any other type of problem: the basic idea is that in addition to the third output 206-3 which is based on all the information additional outputs 206-1, 206-2 are produced in which selectively some types of imaging techniques are removed from the underlying input. Specifically, each output is associated with a specific region of the human organ (here: first output 206-1 with the peripheral zone, PZ, and second output 206-2 with the transition zone, TZ).

When then each such specific region is associated with a particular imaging technique, then at least some of the other imaging techniques, and preferably all of the other imaging techniques, which are not specifically associated with that region, are removed from the underlying input, i.e. are replaced by blanks. Then, for each such specific region a corresponding loss function term of the total loss function is calculated which takes into account only the pixels or voxels within the corresponding specific region and which penalizes differences between the third output 206-3 and the output associated with the specific region.

Thus, the $L_{BCE}$ term will drive the updates of the ANN 204 towards identity with the ground truth, wherein the other, additional loss functions within the total loss function will drive the ANN 204 towards becoming better at determining abnormalities within the respective corresponding regions based on the dominant imaging technique for the regions.

The updating of the parameters of the ANN 204 is repeated for as long as desired in order to then provide the ANN 204 as an artificial intelligence entity, AIE, for determining lesions.

Figure 7:
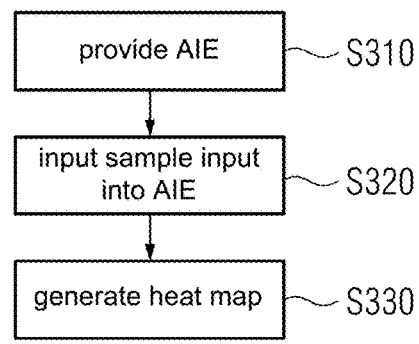
FIG. 7 shows a schematic flow diagram illustrating another method for detecting abnormalities within medical imaging data according to an exemplary embodiment.

FIG. 7 shows a schematic flow diagram illustrating a method for detecting abnormalities in medical imaging data of a human organ, in particular a prostate.

In a step S310, an artificial intelligence entity, AIE, is provided according to the method as it has been described with respect to FIG. 5 and FIG. 6. In a step S320, an input sample is input into the artificial intelligence entity, AIE, such as trained ANN 204 wherein the input sample comprises first imaging results 202-1 from a DWI scan, and second imaging results 202-2 from a T2W scans, as well as mask information 202-3, e.g. in form of two mask channels, one for the transition zone, TZ, and one for the peripheral zone, PZ, as described in the foregoing. As a result, an abnormality heat map 228 is generated (S330) as the output of the artificial intelligence entity, AIE, which may in particular be a probability heat map of the entire prostate. In this variant, no late fusion is needed to combine different feature maps.

Figure 8:
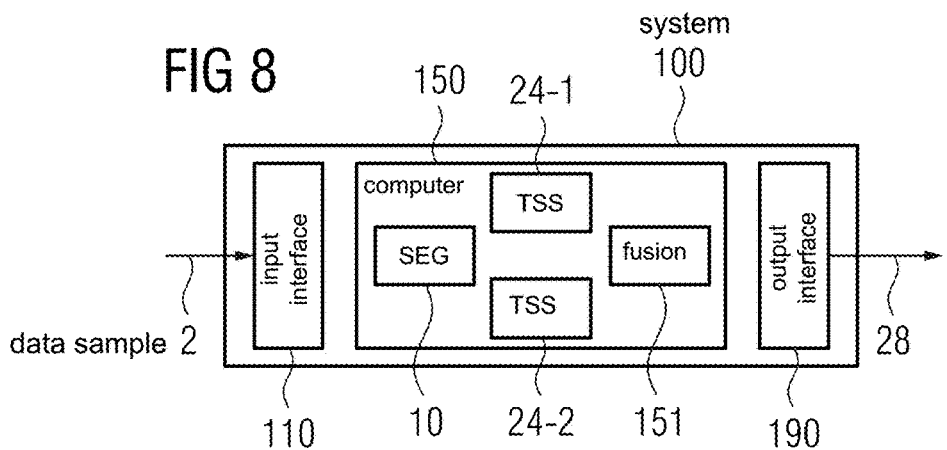
FIG. 8 shows a schematic block diagram illustrating a system according to an exemplary embodiment.

FIG. 8 shows a schematic block diagram illustrating a system 100 according to an embodiment of the third aspect of the present disclosure, i.e. a system 100 for detecting abnormalities such as lesions in medical imaging data of a human organ, in particular a prostate. The system 100 is in particular suited for performing the method as it has been described with respect to FIG. 3 and FIG. 4. Thus, the system 100 can be realized with any of the details, variants or modifications as have been described with respect to the method according to FIG. 3 and FIG. 4 and vice versa.

The system 100 comprises an input interface 110 for receiving a data sample 2 comprising a plurality of imaging results for the human organ, in particular prostate, from different types of imaging techniques. The data sample 2 may be provided to the input interface 110, and received thereby, directly from a medical imaging device such as an MR scanner and/or it may be provided from a medical imaging results repository, such as a picture archiving and communication system, PACS.

The system further comprises a computing device (computer) 150 configured to implement a trained artificial intelligence entity, AIE, (in particular a trained artificial neural network, ANN), comprising a first trained sub-structure 24-1, a second trained sub-structure 24-2, and a fusion module 151. The first and the second trained sub-structures 24-1, 24-2 may in particular have been provided by the training method as has been described with respect to FIG. 1 and FIG. 2. In an exemplary embodiment, the computer 150 includes processor circuitry that is configured to perform one or more functions and/or operations of the computer 150.

The first trained sub-structure 24-1 is configured and trained to receive the data sample 2 from the input interface 110 and to provide, as its output based thereon, a first intermediate spatial feature map 26-1. The second trained sub-structure 24-2 is configured and trained to receive the same data sample 2 from the input interface 110 and to provide, as its output based thereon, a second intermediate spatial feature map 26-2.

The fusion module 151 is configured to generate S140 an abnormality heat map 28 by taking pixels or voxels for the second spatial region from the first intermediate spatial feature map 26-1 and by taking pixels or voxels for the first spatial region from the second intermediate spatial feature map 26-2 such that the abnormality heat map 28 comprises pixels or voxels for the first and the second spatial region.

The system 100 also comprises an output interface 190 for outputting at least the generated abnormality heat map 28.

Optionally, the computing device 150 is further configured to implement a trained artificial intelligence segmentation entity 10 configured and trained for receiving the data sample 2 as its input and to output a segmentation 12 as its output based thereon. The fusion module 151 may then be configured to take the pixels or voxels based on the segmentation 12 for the generating S140 of the abnormality heat map 28.

Figure 9:
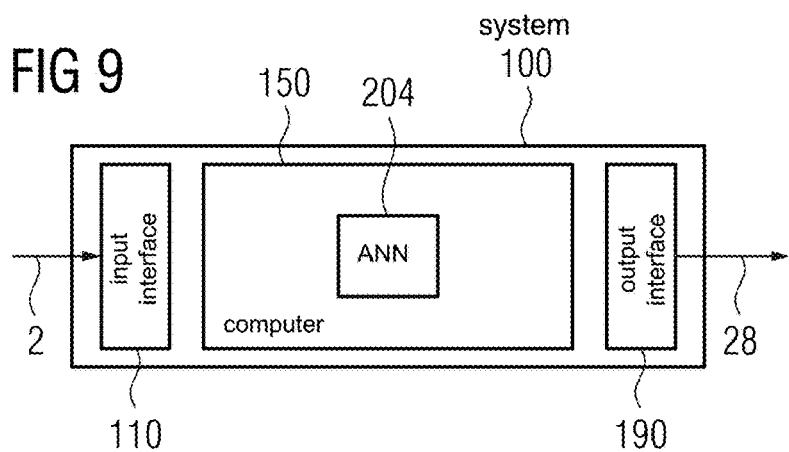
FIG. 9 shows a schematic block diagram illustrating a system according to an exemplary embodiment.

FIG. 9 shows a schematic block diagram illustrating a system 100 according to an embodiment of the fourth aspect of the present disclosure, i.e. a system 100 for detecting abnormalities such as lesions in medical imaging data of a human organ, in particular a prostate. The system 100 is in particular suited for performing the method as it has been described with respect to FIG. 7. Thus, the system 100 can be realized with any of the details, variants or modifications as have been described with respect to the method according to FIG. 7 and vice versa.

Accordingly, the system 100 according to FIG. 9 comprises an input interface 110, an output interface 190 and a computing device (computer) 150 as it has been described with respect to FIG. 8, with the difference that the computing device 150 is configured to implement the trained ANN 204 trained using the method as described with respect to FIGS. 5 and 6. In an exemplary embodiment, the computer 150 includes processor circuitry that is configured to perform one or more functions and/or operations of the computer 150.

The trained ANN 204 is configured and trained to receive the data sample 2 from the input interface 110 and to provide, as its output based thereon, an abnormality heat map 28.

Figure 10:
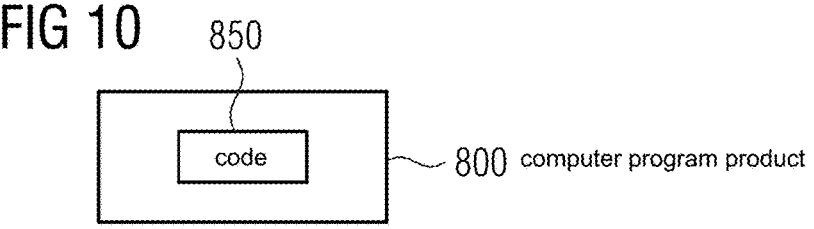
FIG. 10 shows a schematic block diagram illustrating a computer program according to an exemplary embodiment.

FIG. 10 shows a schematic block diagram illustrating a computer program product 800 according to an embodiment of the seventh aspect of the present disclosure, i.e. a computer program product 800 comprising executable program code 850 configured to, when executed by a computing device 150 perform the method according to any embodiment of the first aspect of the present disclosure or according to any embodiment of the second aspect of the present disclosure, in particular any of the methods as described with respect to FIGS. 1 to 7.

Figure 11:
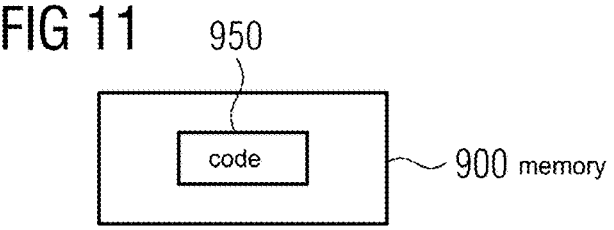
FIG. 11 shows a schematic block diagram illustrating a data storage medium according to an exemplary embodiment.

FIG. 11 shows a schematic block diagram illustrating a non-transitory, computer-readable data storage medium 900 according to an embodiment of the eighth aspect of the present disclosure, i.e. a data storage medium 900 which comprises program code 950 configured to, when executed by a computing device 150, execute the method according to any embodiment of the first aspect of the present disclosure or according to any embodiment of the second aspect of the present disclosure, in particular any of the methods as described with respect to FIGS. 1 to 7. Such a data storage medium may be, for example, a USB stick, a CD ROM, a DVD ROM, a Blue-Ray Disc, a hard drive, a solid state drive and/or the like.

In the foregoing detailed description, various features are grouped together in the examples with the purpose of streamlining the disclosure. It is to be understood that the above description is intended to be illustrative and not restrictive. It is intended to cover all alternatives, modifications and equivalence. Many other examples will be apparent to one skilled in the art upon reviewing the above specification, taking into account the various variations, modifications and options as described or suggested in the foregoing.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processor circuitry" shall be understood to be circuit(s), processor(s), logic, or a combination thereof. A circuit includes an analog circuit, a digital circuit, state machine logic, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A computer-implemented method for training an artificial intelligence entity (AIE) for detecting abnormalities in medical imaging data of a human organ, the method comprising:
providing medical imaging data of the human organ as training data including training samples, the medical imaging data including a plurality of imaging results from different types of imaging techniques for each training sample of the training data;
providing at least one pre-trained or randomly initialized artificial intelligence entity (AIE); and
training the at least one AIE using the provided training samples, the training including:
in a first sub-step, for at least one training sample, calculating a first loss function for at least a sub-structure of the at least one AIE independently of at least one first spatial region of the human organ, and
in a second sub-step, for at least one training sample, calculating a second loss function for at least a sub-structure of the at least one AIE independently of at least one second spatial region of the human organ,
wherein the at least one AIE is trained using at least the calculated first loss function and the calculated second loss function.

2. The method of claim 1, wherein the at least one first spatial region and the at least one second spatial region are disjunct.

3. The method of claim 2, wherein:
the first loss function is based only on pixels or voxels of the provided medical imaging data within the at least one second spatial region; and
the second loss function is based only on pixels or voxels of the provided medical imaging data within the at least one first spatial region.

4. The method of claim 1, wherein in the first sub-step and in the second sub-step subsequently, the corresponding loss function for the same at least sub-structure of the AIE is calculated.

5. The method of claim 1, wherein:
for the first sub-step, the imaging results from the at least one first type of imaging technique within each training sample of the at least one training sample are replaced by a pre-defined blank before being used for calculating the first loss function, and
for the second sub-step, the imaging results from the at least one second type of imaging technique within each training sample of the same at least one training sample are replaced by the pre-defined blank before being used for calculating the second loss function.

6. The method of claim 5, wherein:
in a third sub-step, a third loss function is calculated for each training sample of the same at least one training sample;
in the third sub-step, each training sample is left unaltered before being used for calculating the third loss function;
the third loss function, when calculated, penalizes differences between an output of the sub-structure of the at least one AIE and corresponding labels for each training sample; and
the sub-structure of the at least one AIE is trained using a total loss function which is based on at least the first loss function, the second loss function, and the third loss function.

7. The method of claim 6, wherein:
the training sample with the imaging results from the at least one first type of imaging technique replaced by the pre-defined blank is input into the sub-structure of the AIE in order to produce a first intermediate spatial feature map;
the training sample with the imaging results from the at least one second type of imaging technique replaced by the pre-defined blank is input into the sub-structure of the AIE in order to produce a second intermediate spatial feature map;
the unaltered training sample is input into the sub-structure of the AIE in order to produce a third intermediate spatial feature map; and
the first loss function, when calculated, penalizes differences between the third intermediate spatial feature map and the first intermediate spatial feature map, and the second loss function penalizes differences between the third intermediate spatial feature map and the second intermediate spatial feature map.

8. The method of claim 1, further comprising pre-training the sub-structure of the at least one AIE and cloning the sub-structure of the at least one AIE to obtain a first pre-trained sub-structure and a second pre-trained sub-structure, wherein:
the first sub-step comprises training the first pre-trained sub-structure using the first loss function to obtain a first trained sub-structure; and
the second sub-step comprises training the second pre-trained sub-structure using the second loss function to obtain a second trained sub-structure.

9. A non-transitory computer-readable storage medium with an executable program stored thereon, that when executed, instructs a processor to perform the method of claim 1.

10. A computer-implemented method for detecting abnormalities in medical imaging data of a human organ, the method comprising:
providing a first trained sub-structure and a second trained sub-structure;
inputting a data sample comprising a plurality of imaging results for the human organ from different types of imaging techniques into the first trained sub-structure in order to generate a first intermediate spatial feature map;
inputting the same data sample into the second trained sub-structure in order to generate a second intermediate spatial feature map; and
generating an abnormality heat map based on the generated first intermediate spatial feature map and the generated second intermediate spatial feature map,
wherein generating the abnormality heat map includes taking pixels or voxels for a second spatial region of the human organ from the first intermediate spatial feature map and taking pixels or voxels for a first spatial region of the human organ from the second intermediate spatial feature map such that the abnormality heat map comprises pixels or voxels for the first and the second spatial regions.

11. The method of claim 10, wherein providing the first trained sub-structure and the second trained sub-structure comprises:
providing medical imaging data of the human organ as training data including training samples, the medical imaging data including a plurality of imaging results from different types of imaging techniques for each training sample of the training data;

providing at least one pre-trained or randomly initialized artificial intelligence entity (AIE);
pre-training at least a sub-structure of the at least one AIE and cloning the at least sub-structure of the at least one AIE to obtain a first pre-trained sub-structure and a second pre-trained sub-structure; and
training the at least one AIE using the provided training samples, the training including:
in a first sub-step, for at least one training sample, calculating a first loss function for at least a sub-structure of the at least one AIE independently of at least one first spatial region of the human organ, and training the first pre-trained sub-structure using the first loss function to obtain a first trained sub-structure; and
in a second sub-step, for at least one training sample, calculating a second loss function for at least a sub-structure of the at least one AIE independently of at least one second spatial region of the human organ, and training the second pre-trained sub-structure using the second loss function to obtain a second trained sub-structure,
wherein the at least one AIE is trained using at least the calculated first loss function and the calculated second loss function.

12. The method of claim 10, further comprising providing a segmentation for identifying at least the first spatial region and the second spatial region within the input data sample, wherein the pixels or voxels are taken from the first intermediate spatial feature map and the second intermediate spatial feature map, respectively, based on the segmentation.

13. The method of claim 12, wherein the segmentation is automatically provided by inputting the data sample into a trained artificial intelligence segmentation entity, or wherein the data sample comprises at least one segmentation mask.

14. The method of claim 10, wherein the human organ is a prostate.

15. A non-transitory computer-readable storage medium with an executable program stored thereon, that when executed, instructs a processor to perform the method of claim 10.

16. A system for detecting abnormalities in medical imaging data of a human organ, the system comprising:
an input interface configured to receive a data sample including a plurality of imaging results for the human organ from different types of imaging techniques;
a computer configured to implement a trained artificial intelligence entity (AIE) including:
a first trained sub-structure configured and trained to receive the data sample from the input interface and to provide, as its output based thereon, a first intermediate spatial feature map;
a second trained sub-structure configured and trained to receive the same data sample from the input interface and to provide, as its output based thereon, a second intermediate spatial feature map; and
a fusion module configured to generate an abnormality heat map by taking pixels or voxels for a second spatial region of the human organ from the first intermediate spatial feature map and by taking pixels or voxels for a first spatial region of the human organ from the second intermediate spatial feature map such that the abnormality heat map includes pixels or voxels for the first and the second spatial regions; and
an output interface configured to output at least the generated abnormality heat map.

17. The system of claim 16, wherein the computer is further configured to implement a trained artificial intelligence segmentation entity configured and trained to receive the data sample as its input and to output a segmentation as its output based thereon, and wherein the fusion module is configured to take the pixels or voxels based on the segmentation for the generating of the abnormality heat map.

18. The system of claim 16, wherein the AIE is a trained artificial neural network (ANN).

19. The system of claim 16, wherein the human organ is a prostate.

* * * * *